(12) United States Patent
Filipczak

(10) Patent No.: US 6,467,950 B1
(45) Date of Patent: Oct. 22, 2002

(54) DEVICE AND METHOD TO MEASURE MASS LOSS RATE OF AN ELECTRICALLY HEATED SAMPLE

(75) Inventor: Robert A. Filipczak, Linwood, NJ (US)

(73) Assignee: The United States of America as represented by the Department of Transportation, Washington, DC (US)

( * ) Notice: Subject to any disclaimer, the term of this patent is extended or adjusted under 35 U.S.C. 154(b) by 0 days.

(21) Appl. No.: 09/912,328

(22) Filed: Jul. 26, 2001

(51) Int. Cl.[7] ............................................. G01N 25/00
(52) U.S. Cl. ...................................... 374/14; 73/61.76
(58) Field of Search .............................. 374/14, 10–12, 374/8; 436/147, 155, 156; 73/61.76, 61.77

(56) References Cited

U.S. PATENT DOCUMENTS 6,037,574 A * 3/2000 Lanham et al. ............. 219/544
6,336,741 B1 * 1/2002 Blaine .......................... 374/14

FOREIGN PATENT DOCUMENTS

JP          0163448    * 12/1980 ..................... 374/8

* cited by examiner

Primary Examiner—Christopher W. Fulton
Assistant Examiner—Gail Verbitsky
(74) Attorney, Agent, or Firm—James J. Drew; Otto M. Wildensteiner

(57) ABSTRACT

A device and a method for measuring the mass loss rate of a sample of combustible material placed on a mass-sensitive platform. The material has been formed into a block through which a heating wire has been inserted that thermally degrades the block when an electric current is passed through the embedded wire. Because the terminal ends of the embedded wire deform when heated, attachments that supply the current to these terminals exert spurious forces on the block resulting in inaccurate mass measurements. To eliminate these forces, the terminal ends of the heating wire are connected to high conductivity leads that are dipped into electrically insulated reservoirs of a conductive fluid, typically mercury, to which a power supply provides a potential difference. As the terminal ends of the heating wire deform under the resulting current, the leads are free to move in the conductive fluid without exerting any forces on the block, allowing the true mass loss rate of the sample to be measured.

20 Claims, 1 Drawing Sheet

DEVICE AND METHOD TO MEASURE MASS LOSS RATE OF AN ELECTRICALLY HEATED SAMPLE

The invention described herein may be manufactured, used, and licensed by or for the Government of the United States without the payment to me of any royalties thereon.

FIELD OF THE INVENTION

The present invention relates generally to the measurement of mass loss rate of samples undergoing thermal decomposition caused by electrical heating, and more particularly to measurements where the forces exerted by the electrical leads on the sample are minimized through the use of frictionless contacts. Minimizing such external forces make the mass loss rate measurements more accurate. Such measurements are useful in determining flammability parameters of large size samples, typically 50 to 100 grams, of combustible materials.

BACKGROUND OF THE INVENTION

Manufacturers of fire detectors for commercial aircraft are seeking to shorten detection times, improve reliability, and enhance specificity using multi-sensor arrays and advanced logic. To facilitate this effort in the area of aircraft cargo compartment fire detection, the Federal Aviation Administration (FAA) has developed and characterized a reproducible smoke generation source consisting of several pure polymers (plastics) found in articles of luggage. The typical test specimen, which is the subject of a separate patent application, is a 10×10×1 cm plaque thermoformed from natural, unfilled plastic pellets by compression molding and containing an embedded Nichrome™ heating wire. The level and duration of smoke production are determined by the electrical current to the heating wire in the specimen. Flaming combustion can be initiated at any time during the test using a spark igniter, with the rate of heat release controlled by varying the current to the heating wire. Using a fire calorimeter, a specimen can be tested to determine mass loss rate, heat release rate, smoke density and morphology, and the concentrations, over time, of various combustion gases in both flaming and non-flaming events.

Accurate mass loss measurements during the tests are not feasible, however, because the bending stiffness and thermal expansion of the electrical wires connecting the test specimen to the power source produce large spurious forces on the load transducer that continuously measures the mass of the sample. These forces are unrelated to the specimen mass loss history and have to be eliminated or minimized to accurately measure the mass loss rate.

OBJECTS OF THE INVENTION

Accordingly, it is an object of the present invention to provide a means and method for accurately measuring the mass loss rate of thermally decomposing materials where the decomposition event is caused by electrically heating the material.

It is a further object of the present invention to provide a means and method for accurately measuring the mass loss rate of thermally decomposing materials by supplying electrical power to the material without exerting outside forces on the material.

It is a still further object of the present invention to provide a means and method for measuring the mass loss rate of thermally decomposing materials by supplying electrical power to the material through frictionless electrical contacts.

SUMMARY

Briefly, the present invention measures the mass loss rate of a thermally decomposing material that is heated by means of a heating element embedded in the material. External forces exerted on the sample by the electrical leads distort the mass measurement and produce inaccurate results. To minimize these external forces, the leads are connected to copper wires that extend downward into cups of liquid mercury contained in separate brass cups electrically connected to a power supply. The copper wires descending from the leads touch nothing but the mercury from which it receives the electrical current. The buoyant force of the mercury on the copper wire and the heat loss to the mercury and the copper leads are negligible.

DETAILED DESCRIPTION

Figure 1:
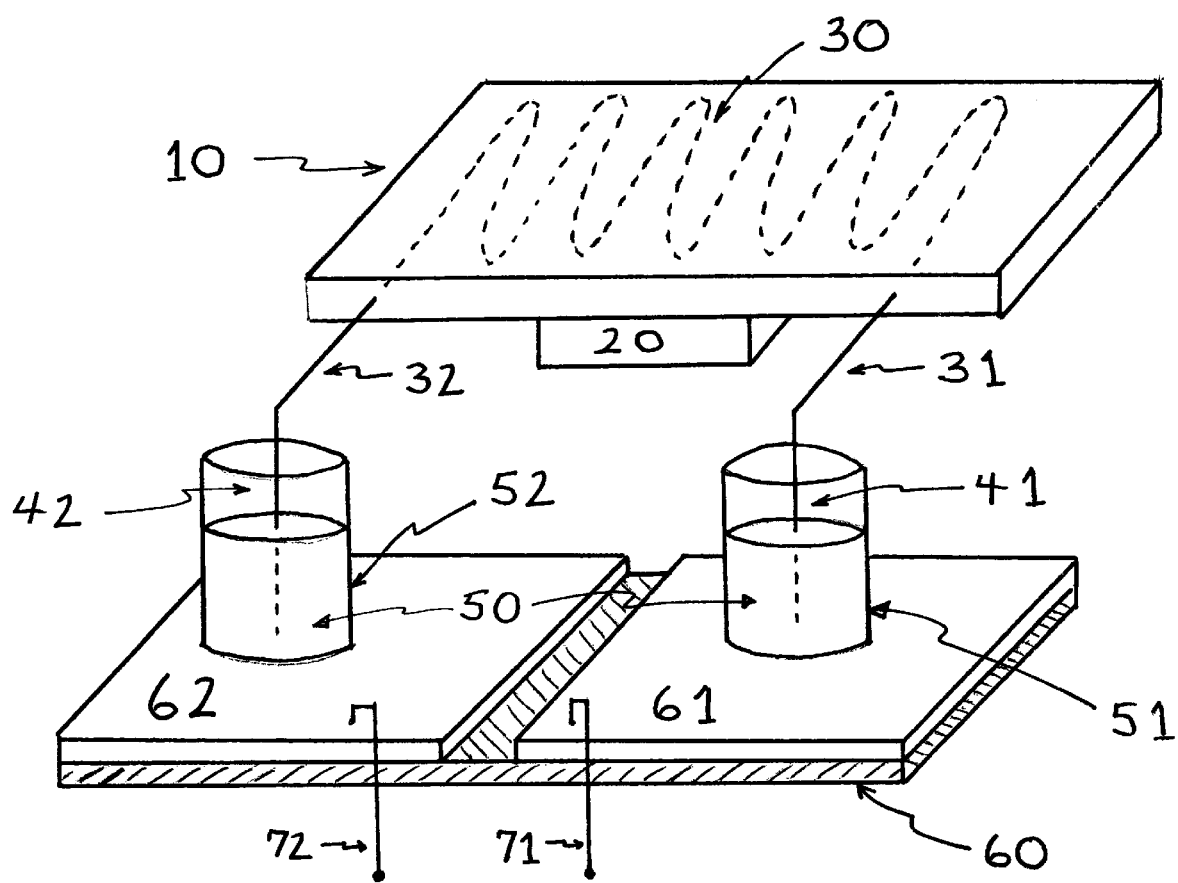
FIG. 1 is an idealized representation of one embodiment of the invention illustrating the test sample with embedded heating element mounted on a mass transducer, or scale, to measure the mass loss rate. Also illustrated are the frictionless contacts that provide electrical power to the heating element.

Sample 10, typically a block of mass 70 grams or so, is mounted on a mass-sensitive platform, or scale, 20 that can continuously measure the mass of sample 10. Nichrome™ wire leads 31 and 32, each approximately 0.025 inches in diameter, protrude from sample 10 to conduct electricity from a power source into heating element 30. When supplied with an electrical current, Nichrome™ heating element 30, embedded in sample 10, heats sample 10 to cause its thermal decomposition. Two rectangular pieces of copper sheet, 61 and 62, about ¾×1 inches across and 0.0255 in. thick are placed next to each other, separated about an inch, and fastened to insulated support 60. A section of ⅜ inch diameter copper tubing about an inch and a half long is silver soldered to each copper sheet 61 and 62 to form cups 51 and 52, respectively. Cups 51 and 52 are each filled about three-quarters full of mercury 50. Cups 51 and 52 are fixed in place next to scale 20, but are physically isolated from it. Copper wires 41 and 42 are connected to leads 31 and 32, respectively, and extend downward in an essentially vertical position. Wire 41 is dipped into the mercury in cup 51; wire 42 is dipped into the mercury in cup 52. So positioned, wires 41 and 42 touch nothing but the mercury in their respective cups 51 and 52.

The high conductivity of copper insures that there is little heating of wires 41 and 42, and consequently, little heating of the mercury as electrical current flows through heating element 30. Heating mercury is to be avoided since its toxicity increases when it is heated, creating a health hazard. Gold, silver, aluminum or other high conductivity metal wires could be substituted for copper wires 41 and 42. While liquid mercury is the conductor of choice in the cups, there are other high conductivity fluids to be considered. For example, low melting point metals, such as tin or bismuth, that have less toxic vapor than liquid mercury, may be used. One simple approach would be to wrap the cups in lab heating tape, for example Thermoline/BriskHeat™ heating tape, which can reach temperatures of about 460 C when supplied with an electrical current. Since tin melts at 230 C, and bismuth at 270 C, no special oven, or heated enclosure, is needed.

Wire leads 71 and 72 are attached to copper sheets 61 and 62, respectively, to connect them to a current or voltage source. While a source of direct current may be used, the typical voltage source, a Variac™, can be set anywhere from zero to about 140 volts a.c. Set at approximately 42 volts, the Variac™ provides an alternating electric current through wire leads 71 and 72, to copper sheets, 61 and 62, to the mercury in cups 51 and 52, to the wires 41 and 42, to the leads 31 and 32 and into the heating element 30. While wire leads 71 and 72 are connected as described, other ways of establishing a potential difference between the mercury in cups 51 and 52 can be imagined. For instance, cups 51 and 52 could be directly connected to the Variac™, or if the cups are formed from an insulating material, terminals could be inserted into the respective pools of mercury to conduct the electrical current. As leads 31 and 32 are distorted by the heating process, copper wires 41 and 42 are free to move in the mercury, either side to side or up and down without imparting any force to sample 10 and consequently to scale 20 on which sample 10 rests during testing.

Many other modifications and variations of the present invention are possible in the light of the above teachings. Within the scope of the appended claims, the invention may be practiced otherwise than as specifically described.

I claim:

1. An apparatus for measuring the mass loss of a sample undergoing thermal decomposition caused by an electric current introduced into said sample through a first and a second conductive lead projecting therefrom, said apparatus comprising:
   a. a mass-sensitive platform supporting said sample, said platform providing a signal indicating the mass of the sample supported;
   b. a first reservoir adjacent to said platform and containing a conductive fluid;
   c. a second reservoir adjacent to said platform and containing a conductive fluid;
   d. said first and second reservoirs electrically insulated from each other;
   e. said first conductive lead inserted into said conductive fluid contained in said first reservoir such that said first conductive lead is in contact only with said conductive fluid;
   f. said second conductive lead inserted into said conductive fluid contained in said second reservoir such that said second conductive lead is in contact only with said conductive fluid;
   g. means for accepting a potential difference between the conductive fluid in said first reservoir and the conductive fluid in said second reservoir such that an electrical current may flow from the conductive fluid in said first reservoir to said first conductive lead into said sample and thence from said second conductive lead into said conductive fluid contained in said second reservoir.

2. The apparatus as in claim 1 wherein said conductive fluid is mercury.

3. The apparatus as in claim 1 wherein said conductive fluid is tin, and said first and second reservoirs are maintained at a temperature at or above the melting point of tin.

4. The apparatus as in claim 1 wherein said conductive fluid is bismuth, and said first and second reservoirs are maintained at a temperature at or above the melting point of bismuth.

5. An apparatus for measuring the mass loss of a sample undergoing thermal decomposition caused by an electric current introduced into said sample through a first and a second conductive lead projecting outward therefrom, said apparatus comprising:
   a. a mass-sensitive platform for supporting said sample, said platform providing a signal indicating the mass of the sample supported;
   b. a first high conductivity wire electrically connected to and projecting downward from said first conductive lead;
   c. a second high conductivity wire electrically connected to and projecting downward from said second conductive lead;
   d. a first reservoir adjacent to said platform and containing a conductive fluid;
   e. a second reservoir adjacent to said platform and containing a conductive fluid;
   f. said first and second reservoirs electrically insulated from each other;
   g. said first high conductivity wire inserted into said conductive fluid contained in said first reservoir such that said first high conductivity wire is in contact only with said conductive fluid;
   h. said second high conductivity wire inserted into said conductive fluid contained in said second reservoir such that said second high conductivity wire is in contact only with said conductive fluid;
   i. means for accepting a potential difference between the conductive fluid in said first reservoir and the conductive fluid in said second reservoir such that an electrical current may flow from the conductive fluid in said first reservoir to said first high conductivity wire into said first conductive lead and into said sample and thence from said second conductive lead into said second high conductivity wire into the conductive fluid contained in said second reservoir.

6. The apparatus as in claim 5 wherein said conductive fluid is mercury.

7. The apparatus as in claim 5 wherein said conductive fluid is tin and said first and second reservoirs are maintained at a temperature at or above the melting point of tin.

8. The apparatus as in claim 5 wherein said conductive fluid is bismuth and said first and second reservoirs are maintained at a temperature at or above the melting point of bismuth.

9. A method for measuring the mass loss rate of a sample undergoing thermal decomposition caused by an electric current flowing through an embedded heating wire terminating in a first and a second conductive lead projecting from said sample, said method comprising the steps of
   a. supporting said sample on a mass-sensitive platform that provides a measurement of the mass of said sample;
   b. positioning a first reservoir containing a conductive fluid adjacent to said mass-sensitive platform;
   c. positioning a second reservoir containing a conductive fluid adjacent to said mass-sensitive platform;
   d. electrically insulating said first and second reservoirs from each other;
   e. dipping said first conductive lead into said conductive fluid in said first reservoir such that no part of said first conductive lead touches any part of said first reservoir;
   f. dipping said second conductive lead into said conductive fluid in said second reservoir such that no part of said conductive lead touches any part of said second reservoir;
   g. providing a voltage difference to said conductive fluid in said first reservoir and said conductive fluid in said second reservoir; and, h. measuring the mass of said sample as a function of time.

10. The method as in claim 9 wherein said conductive fluid is mercury.

11. The method as in claim 10 wherein the conductive fluid is tin and said first and second reservoirs are maintained at a temperature at or above the melting point of tin.

12. The method as in claim 10 wherein the conductive fluid is bismuth and said first and second reservoirs are maintained at a temperature at or above the melting temperature of bismuth.

13. A method for measuring the mass loss rate of a sample undergoing thermal decomposition caused by an electric current introduced into said sample through a first and a second conductive lead projecting therefrom, said method comprising the steps of:
   a. supporting said sample on a mass-sensitive platform that provides a measurement of the mass of said sample;
   b. positioning a first reservoir containing a conductive fluid adjacent to said mass-sensitive platform;
   c. positioning a second reservoir containing a conductive fluid adjacent to said mass-sensitive platform;
   d. electrically insulating said first and second reservoirs from each other;
   e. dipping said first conductive lead into said conductive fluid in said first reservoir such that no part of said first conductive lead touches any part of said first reservoir;
   f. dipping said second conductive lead into said conductive fluid in said second reservoir such that no part of said conductive lead touches any part of said second reservoir;
   g. providing a voltage difference to said conductive fluid in said first reservoir and said conductive fluid in said second reservoir; and,
   h. measuring the mass of said sample as a function of time.

14. The method as in claim 13 wherein said conductive fluid is mercury.

15. The method as in claim 13 wherein said conductive fluid is tin and said first and second reservoirs are maintained at a temperature at or above the melting point of tin.

16. The method as in claim 13 wherein said conductive fluid is bismuth and said first and second reservoirs are maintained at a temperature at or above the melting point of bismuth.

17. A method for measuring the mass loss rate of a sample undergoing thermal decomposition supported by an electric current introduced into said sample through a first and a second conductive lead projecting outward therefrom, said method comprising the steps of:
   a. supporting said sample on a mass-sensitive platform that provides a measurement of the mass of said sample;
   b. positioning a first reservoir containing a conductive fluid adjacent to said mass-sensitive platform;
   c. positioning a second reservoir containing a conductive fluid adjacent to said mass-sensitive platform;
   d. electrically insulating said first and second reservoirs from each other;
   e. electrically connecting a first high conductivity wire to said first conductive lead such that said first high conductivity wire projects downward from said first conductive lead;
   f. dipping said first high conductivity wire into said conductive fluid in said first reservoir such that no part of said first high conductivity wire touches any part of said first reservoir;
   g. dipping said second high conductivity wire into said conductive fluid in said second reservoir such that no part of said high conductivity wire touches any part of said second reservoir;
   h. providing a voltage difference between said conductive fluid in said first reservoir and said conductive fluid in said second reservoir; and,
   i. measuring the mass of said sample as a function of time.

18. The method as in claim 17 wherein said conductive fluid is mercury.

19. The method as in claim 17 wherein said conductive fluid is tin and said first and second reservoirs are maintained at a temperature at or above the melting point of tin.

20. The method as in claim 17 wherein said conductive fluid is bismuth and said first and second reservoirs are maintained at a temperature at or above the melting point of bismuth.

* * * * *